United States Patent [19]

Walker

[11] 4,149,414
[45] Apr. 17, 1979

[54] APPARATUS AND METHOD FOR REMOVING SAMPLES FROM FROZEN MEAT BLOCKS

[75] Inventor: Richard B. Walker, Rocky Mount, N.C.

[73] Assignee: United Electric Services, Inc., Rocky Mount, N.C.

[21] Appl. No.: 859,938

[22] Filed: Dec. 12, 1977

[51] Int. Cl.² ............................................. G01N 1/08
[52] U.S. Cl. .................................. 73/424; 73/423 R; 408/42; 408/98; 408/103
[58] Field of Search ................ 73/421 R, 423 R, 424, 73/425, 425.2; 408/42, 52, 98, 103

[56] References Cited

U.S. PATENT DOCUMENTS

| | | | |
|---|---|---|---|
| 2,435,608 | 2/1948 | Sanford et al. | 73/425 |
| 2,559,716 | 7/1951 | Gaudreau | 408/98 X |
| 2,987,922 | 6/1961 | Harrington | 73/425 |
| 3,345,889 | 10/1967 | Yunt et al. | 408/98 |
| 3,492,875 | 2/1970 | Tonjes | 73/424 |
| 4,061,437 | 12/1977 | Strange et al. | 408/42 |

*Primary Examiner*—Charles Gorenstein
*Attorney, Agent, or Firm*—B. B. Olive

[57] ABSTRACT

An apparatus and method for taking a plural number of test samples simultaneously from a frozen meat block packed in a container utilizes a support frame which mounts a fixed table and container clamping device and which supports in sliding relation thereon a movable carriage and multiple drill bit sampling unit. A drive unit, once energized, moves the carriage and multiple drill sampling unit inward or outward by means of a cylinder/piston arrangement connected to the frame at one end and to the carriage at the other. A second motor drive unit drives the multiple drill bits. Means is provided for catching and directing the extracted meat samples to a container situated beneath the sampling drill bits and which moves inward and outward with the carriage as it moves on the support frame.

6 Claims, 10 Drawing Figures

APPARATUS AND METHOD FOR REMOVING SAMPLES FROM FROZEN MEAT BLOCKS

BACKGROUND OF THE INVENTION

1. Field of the Invention

This invention pertains to sampling devices and methods and more particularly to a device and method for simultaneously removing multiple test samples from a frozen block of meat.

2. Description of the Prior Art

Heretofore, as far as applicant is aware, no automatic means of sampling frozen meat blocks has been provided. The present known method is that of taking such samples with a hand-held electric drill. One hole at a time is drilled through a pattern plate containing, say, five guide holes spaced in a manner expected to give a representative collective sample. The sample or shavings are picked up by hand and put into a container for subsequent analysis.

When a meat processor receives a truckload of frozen meat which is to be ground into hamburger, tests have to be run on the meat to determine the fat content of the load. Manufacturers and and suppliers must meet USDA controls over the amount of fat in their hamburger meat. Therefore, a truck loaded with meat and delivered to the processor may contain, for example, 50 pallets, each holding up to 25 containers or boxes of meat per pallet. As the truck is unloaded, a sample box is removed from each pallet so that a 50-pallet truckload would have 50 boxes of meat removed. These 50 boxes are typically drilled and tested by the manufacturer on its premises or in the event of dispute a certified laboratory is employed for the drilling and testing. Approximately five samples are drilled from each of the frozen boxes of meat, one hole at a time. The resulting samples are collected from each hole, transferred to a container, combined and such sample meat is tested to see if that particular load of meat meets the USDA fat content requirements.

One of the obvious disadvantages to the present hand drill method of sampling is the amount of time involved in obtaining the required number of samples as previously described. A further disadvantage is the amount of handling of the meat required by the existing method of gathering the samples or shavings by hand and placing them in a container. The use of a pattern plate introduces sanitation considerations. Also, differing box sizes are not readily accommodated. Thus, the object of the present invention apparatus and method is to overcome these and other disadvantages of the present system and method.

SUMMARY OF THE INVENTION

The apparatus and method of the present invention is directed to removing and collecting plural samples simultaneously from frozen meat blocks. A support frame rigidly mounts at the front end thereof a support table for receiving the frozen meat container or box, each of which typically weighs approximately 60 pounds. Upright abutment members are mounted at both rearward edges of the support table to provide a fixed vertical alignment and stop for the face of the contained block to be sampled. Each abutment member has a forwardly-spaced, loosely-mounted pivotal clamping device mounted thereon so that once a container is placed on the support table and the face of the block to be drilled is uncovered and pushed forward against the abutment members, the clamping devices can be loosely engaged against the back of the container to hold the container in place during the sampling process. The clamping devices are designed such that the drilling or sampling operation tends to bind the clamping devices and, thus, insures positive securement during sampling but with ease of release after sampling. A range of box sizes is accommodated.

The apparatus control panel is positioned below and at the front of the support table so that a single operator can run the test apparatus as well as place the containers on the support table and remove them when testing is complete. A pair of guide channels are rigidly mounted on the support frame. A multiple drill bit unit is mounted on a carriage which, in turn, is slidably mounted on the guide channels by means of a pair of plastic runners secured to the base of the drill bit unit. A hydraulic drive unit is mounted on the support frame beneath the drill bit unit and a piston/cylinder arrangement is energized by this hydraulic drive unit to control forward and backward movement of the drill bit unit. A motor and gear drive unit is mounted on the carriage and when energized causes rotation of the multiple drill bits as the carriage with the drill unit is moved towards the container and the bits penetrate the meat block to remove the samples. A limit switch arrangement controls forward and return limits of the carriage and drill bit unit. A guide funnel is removably secured to the face of the drill bit unit so that as sample meat is removed by the multiple bits it automatically drops into this funnel for delivery into a bag or other receptacle below the tray ready for immediate testing.

DESCRIPTION OF THE PREFERRED EMBODIMENT

Turning now to a detailed description of the invention apparatus and method for removing samples from frozen meat blocks, the apparatus 10 for removing frozen meat samples from meat blocks generally comprises a frame 11; a frozen meat block container receiving table 12; container clamping means 13, 14; movable carriage 15; multiple drill bit unit 16 and sample receiving means 17.

Support frame 11 is preferably made from stainless steel square tubing which is continuous welded and polished at all joints to facilitate cleaning after use. Frame 11 has integral legs 19 and at the four bottom corners of legs 19 are mounted four adjustable glides 20. Glides 20 allow apparatus 10 to be leveled on all surfaces by screwing glides 20 in or out. Container receiving table 12 is made integral with the front end of frame 11 for receiving a container 21, filled with a frozen block of meat, so that container 21 rests on its end with the greatest surface area turned inwards when the top is removed. As with the frame 11, table 12 is continuous welded to frame 11 and polished for cleaning purposes.

Figure 3:
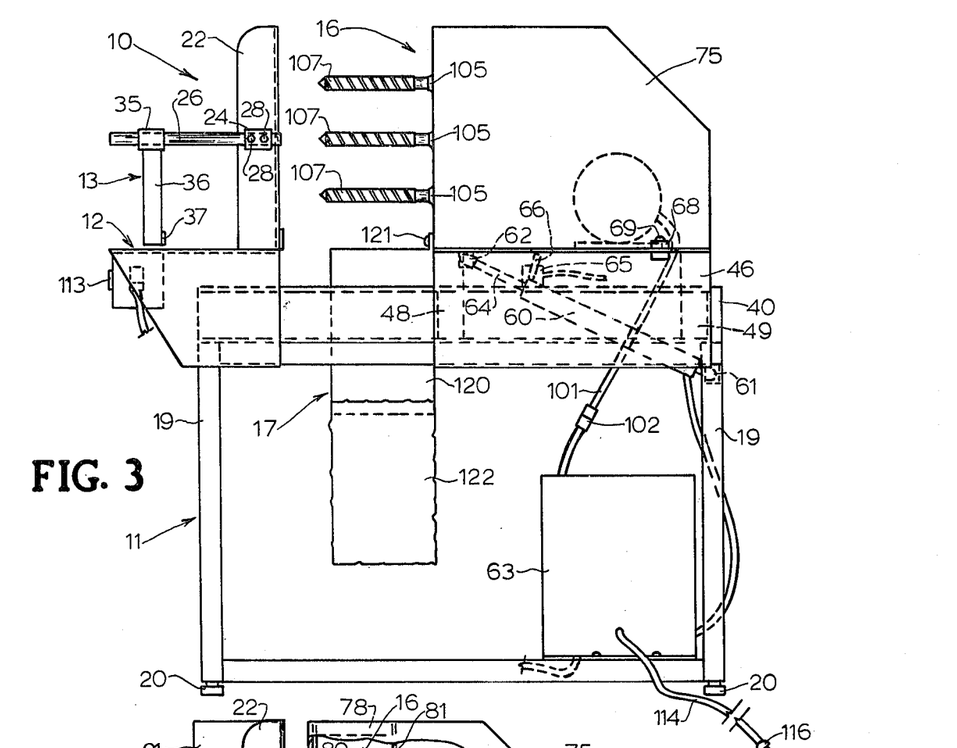
FIG. 3 is a side elevation view of the apparatus of FIGS. 1 and 2.
Figure 4:
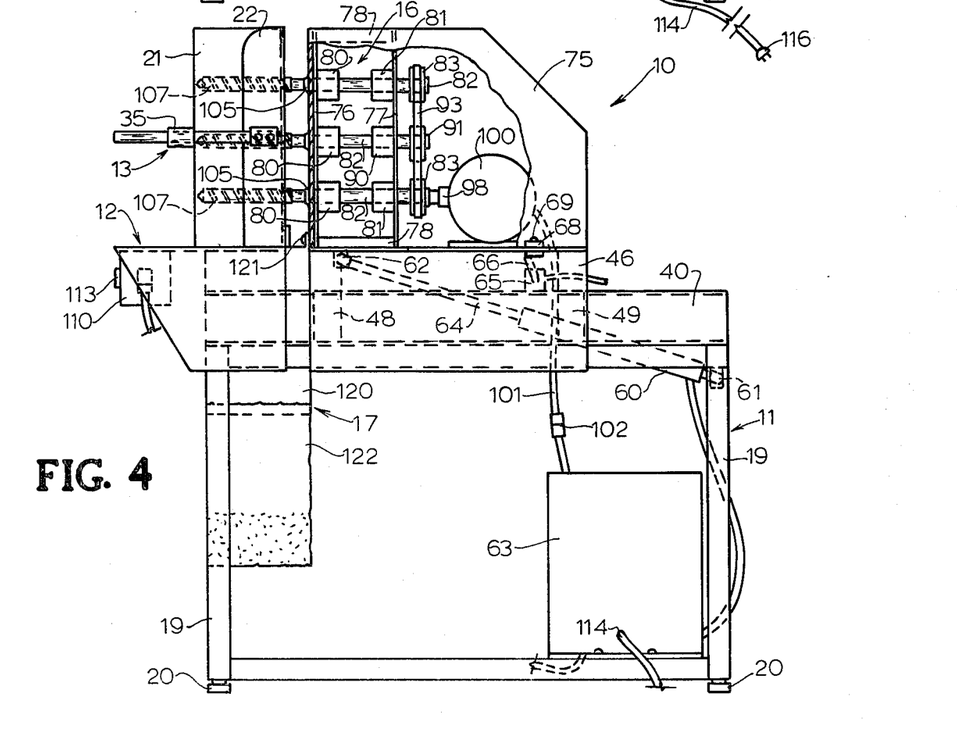
FIG. 4 is a fragmentary side elevation view similar to FIG. 3 but with a frozen meat block container in place, the clamps in clamping position and with the carriage and multiple drill bit unit moved forward illustrating the multiple bits penetrating the meat block and delivering the multiple meat samples into a bag beneath the drill bit unit.
Figure 5:
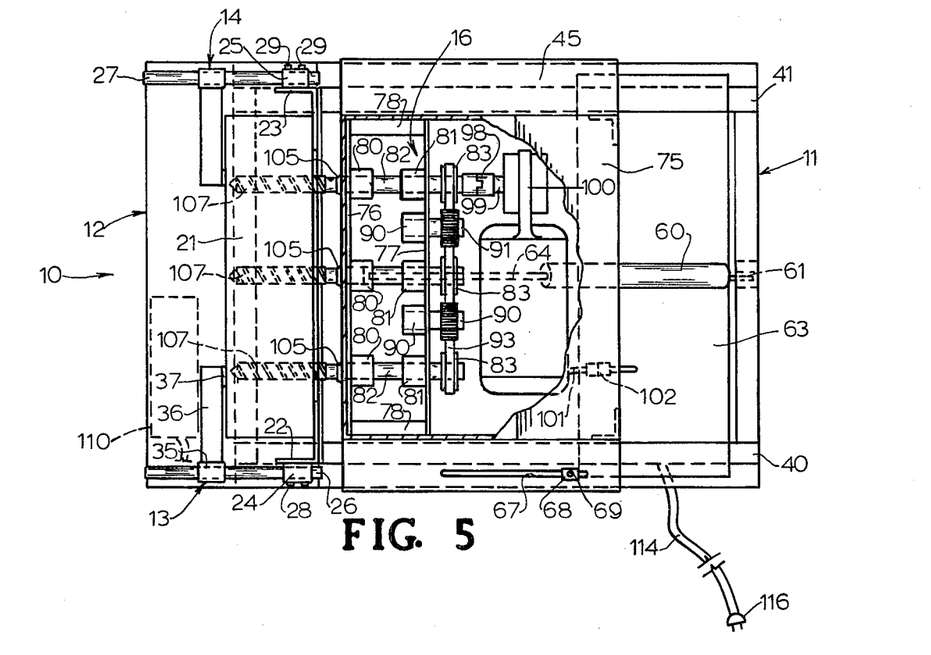
FIG. 5 is a fragmentary top plan view of the apparatus of FIG. 5.

As best seen in FIGS. 3, 4 and 5, support table 12 extends beyond the front edge of frame 11 for ease in placement of container 21 on table 12 by the operator. At the rear of table 12 is a pair of elongated upright right angle abutment members 22, 23 which are provided for vertically aligning the face of the block in container 21 when the block is placed on table 12 for drilling. Since, during the drilling operation, there is a tendency for the container 21 to be forced outwardly in the direction of the drilling, the invention provides for a very simple clamping arrangement which enables container 21 to be clamped during drilling and quickly released after drilling is completed. For this purpose, a pair of sleeves 24, 25 are welded respectively to outer surfaces of abutment members 22, 23 and receive a pair of outwardly extending horizontal rods 26, 27, respectively. Set screws 28 and 29 adjustably mount rods 26, 27 within the respective sleeves 24, 25. Sleeves 24, 25 are rigidly secured on upright abutment members 22, 23 at approximately midway their height. A pair of similar clamps 13, 14 are rotatably mounted on rods 26, 27, respectively. Using clamp 13 as an example, it will be noted that clamp 13 includes a sleeve 35 whose internal diameter is sufficiently large to permit a loose fit and free rotation on rod 26. However, when clamp 13 is put in an angular bind during the drilling operation, sleeve 35 is caused to bind against rod 26 which prevents rotation of the clamp and maintains container 21 in a proper position for drilling. Clamp 13 also includes a rectangular arm 36 which is integrally secured to sleeve 35 and a clamping pad 37 is integrally secured to arm 36. Pad 37 is designed to reside and press against the back of container 21 when the open, exposed front of the container is positioned against abutment members 22, 23 during drilling. The clamp structure 14 is similarly constructed and functions in the same manner.

Since the cardboard wrapper in which container 21 is conventionally packaged has a certain amount of resiliency, the described clamps 13, 14 can be quickly rotated into clamping position as shown in FIGS. 4 and 5 and pressed inwardly tightly against the back of container 21 before drilling proceeds. The inherent resiliency of the cardboard wrapper will tend to hold clamps 13, 14 in their respective clamped positions due to the mentioned binding effect of clamps 13, 14 on rods 26, 27. Then, as the drilling proceeds, this binding effect increases and the clamping effect becomes even more secure. It has also been found that as the drills are withdrawn, the binding effect will cause the clamps 13, 14 to automatically release and drop to the unclamped position, shown in FIGS. 1 and 2, which allows container 21 to be removed from table 12 once drilling has been completed. Also, a range of box sizes can be accommodated.

Turning now to a description of carriage 15, carriage 15 is designed to be guided in its movement by a pair of channel members 40, 41 which are integrally secured to frame 11 by welding. Channel members 40, 41 are U-shaped and have the open ends of the U turned inwardly facing each other. Carriage 15 includes a bed 45 formed of stainless steel plate with downwardly extending vertical sides 46, 47. A pair of angle support brackets 48, 49 are integrally secured below and to the bottom side of bed 45 and are inwardly spaced from side 46. A similar pair of angle brackets 51, 52 are integrally secured to the bottom side of bed 45 and are inwardly spaced from side 47. A plastic bar or runner 55 is integrally secured to angle brackets 48, 49 and slides inside U-shaped channel member 40. A similar plastic runner 56 is integrally secured to angle brackets 51, 52 and glides inside U-shaped channel member 41. Thus, runners 55, 56 slide back and forth inside channel members 40, 41 as carriage 15 is moved back and forth.

Figure 8:
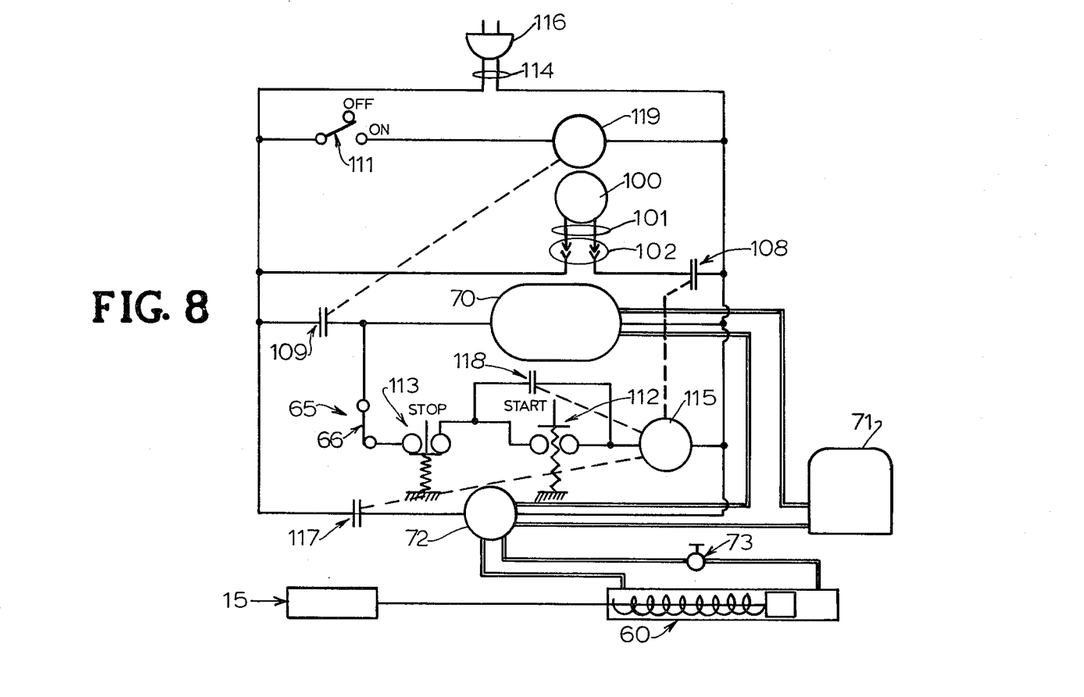
FIG. 8 is an electrical and hydraulic schematic diagram for the apparatus of the invention.

Positioning of carriage 15 is effected by means of a piston and cylinder unit 60. Unit 60 is pivotally connected at the cylinder mounting end to frame 11 by bracket 61 and is connected at the rod end to bracket 62. The piston and cylinder unit 60 may be of conventional construction and in the illustrated embodiment is fluid actuated between advanced and retracted positions. The hydraulic fluid supply is provided and controlled by an integrated unit having a motor driven pump 70, a reservoir 71, an electrically operated hydraulic spring-loaded transfer valve 72, a manual control valve 73, and an appropriate relief valve, not shown. Transfer valve 72 is spring-loaded and when not electrically energized causes transfer of fluid to the front of cylinder unit 60 for movement to a retracted position. Flow valve 73 is connected in series with the inlet line connected to the rear of the cylinder unit 60 as illustrated in FIG. 8 and is used to adjust the flow of fluid and thereby control the forward carriage speed of between zero and any desired maximum value. While various hydraulic systems known to those skilled in the art can be utilized for purposes of the invention, a complete system of the type described and satisfactory for the purpose of the invention is sold by Delta Power Hydraulic Company, 4700 Boeing Dr., Rockford, Ill. 61109, and is identified as the Series B type.

From the description thus far given, it can be seen that as piston rod 64 is moved outward, bed 45 of carriage 15 is caused to be moved toward table 12. Forward and reverse movement of bed 45 is controlled by a limit switch 65 which is fixedly connected to channel member 40 beneath bed 45. Limit switch 65 has a trip arm 66 positioned to engage the lower portion of block 68 mounted in slot 67. Slot 67 extends a predetermined distance along the length of bed 45 parallel with channel member 40 and block 68 is positioned in a predetermined location with respect to slot 67 by loosening or tightening screws 69. Later description is directed to operation of the limit switch 65 in conjunction with the piston cylinder unit 60.

Figure 6:
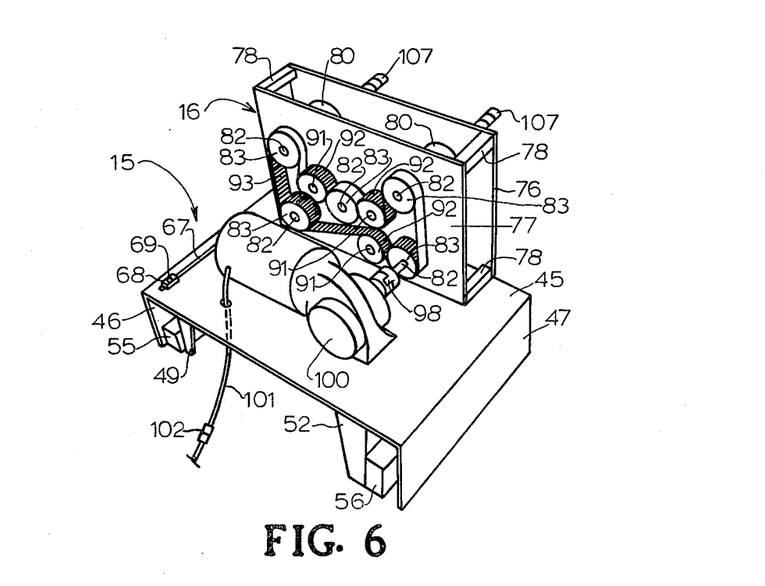
FIG. 6 is a perspective view of the carriage and drill bit unit subassembly as employed in the invention removed from the apparatus and with the subassembly cover removed.
Figure 7:
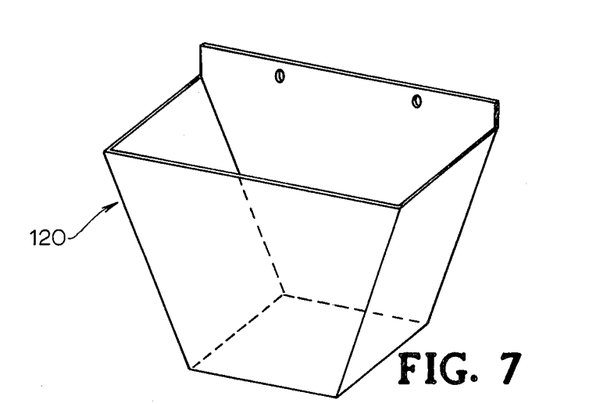
FIG. 7 is a perspective view of the meat sample guide funnel.

The multiple drill bit unit 16 is housed partially by a cover 75 and is secured to bed 45 of carriage 15 at its forward end. A pair of bearing support plates 76, 77 are spaced apart by spacer blocks 78 and a set of five enclosed bearings 80 are secured to the back of plate 76 as best seen in FIGS. 4 and 5. A similar set of five enclosed bearings 81 are secured to the inside surface of plate 77 and five drive shafts 82 rotate within and extend between bearings 80, 81. Five gears 83 are mounted on the driven ends of shafts 82 and are fixedly secured thereto as a means of rotating the shafts. An additional set of three enclosed bearings 90 are secured to the inside surface of plate 77 and an additional set of three idler shafts 91 rotate within bearings 90. Three idler gears 92 are secured to the ends of shafts 91 as best seen in FIG. 6. A suitable mating tooth drive belt 93 connects and drives the sets of gears 83 and 92. A coupling 98 is secured to the end of one of the driven shafts 82 and by means of an extension shaft 99 is integrally secured to coupling 98 and shaft 99 is driven by electric motor 100.

In order to facilitate repairs, routine maintenance, and the like, motor 100 is energized through cord 101 and a quick disconnect plug 102. Thus, all that is required to entirely remove the subassembly illustrated in FIG. 6 is to disconnect plug 102 and the rod end of the cylinder unit 60 from the bracket 62 to which it is connected, as previously explained.

Figure 9:
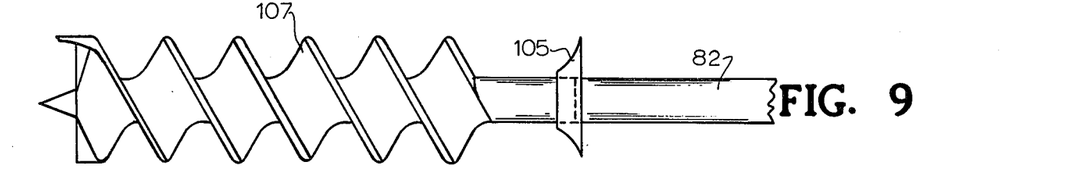
FIG. 9 is a fragmentary side view of a preferred form of drill bit used with the invention.
Figure 10:
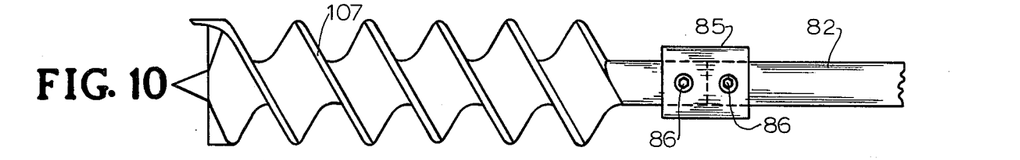
FIG. 10 is a fragmentary side view of another type of a drill bit useful with the invention.

The drill bit preferably takes the form illustrated in FIG. 9 in which the drill flutes 107 are formed integral with the drive shaft 82 and mount an appropriate seal 105 to prevent entry of foreign matter into the drive portion of the drill bit unit 16. Alternatively, connection of the drive shaft 82 to the flute portion 107 of the drill bit may be made through a sleeve 85 having appropriate set screws 86. Stainless steel bits are preferred and flutes 107 should, of course, be adapted to frozen meat drilling operations.

A control panel 110 is positioned beneath and to the front of the receiving table and in a position accessible to the operator. Panel 110 mounts a rotatable selector switch 111 which is normally placed in an on position and left in such on position when a series of frozen meat block containers are to be sampled. Switch 111 in the on position actuates a motor starter 119 and causes contacts 109 to close and energize the hydraulic pump motor 70 but not the drill bit motor 100. Motor 70 will continue to run until the selector switch 111 is returned to the off position. To start carriage advancement and drill rotation, a normally open start button 112 is manually depressed to cause magnetic starter 115 to lock in through one of its normally open contacts 117, 118. Magnetic starter 115 will remain closed until the carriage 15 advances sufficiently to open the normally closed limit switch 65 or until the normally closed stop button 113 is manually depressed.

Once magnetic starter 115 has been placed in a closed position, drill motor 100 will be energized. Also, the electrically-operated hydraulic transfer valve 72 will be energized and positioned so as to direct fluid through the manually positionable flow valve 73 to the rear of the cylinder unit 60 to advance the carriage 15. The amount of fluid transferred to cylinder 60 at this time through transfer valve 72 can, of course, be controlled by positioning of valve 73 and thereby control the speed at which the drill flutes 107 on carriage 15 are advanced into the frozen meat block contents of container 21.

When pressure is applied to the rear of the piston rod portion of cylinder unit 60, it can be seen that the bed 45 of carriage 15 is advanced toward container 21 and simultaneously the multiple drill bit unit 16 is advanced forward toward container 21 and at a speed determined by the positioning of flow valve 73.

Once the multiple drill bit unit 16 has reached some predetermined advanced position which controls the depth of drilling, the trip arm 66 of limit switch 65 will contact a lower surface on the adjustment block 68. This action causes limit switch 65 to open and also causes magnetic starter 115 to open. Once magnetic starter 115 returns to an open position, drill motor 100 will be de-energized as will the hydraulic transfer valve 72. Valve 72 operating under spring loading is now respositioned so as to cause the hydraulic fluid to be directed to the front of the cylinder unit 60 and to return the cylinder unit to a retracted position. This action, of course, causes the carriage 15 and the drill bit unit 16 mounted on bed 45 to retract to the rear of frame 11. However, the drill bits 107 are stopped during such retraction. Once the drill bit unit 16 has been fully retracted, the previously drilled container 21 can thus be safely removed and replaced by another container having another frozen meat block to be sampled. During the drilling operation, the various bits of meat extracted by the five drills will be directed through an appropriate guide funnel 120 which is detachably secured by means of screws 121 to the lower front surface of cover 75. The samples, themselves, are then collected in an appropriate bag or other container 122 for subsequent analysis.

In a typical operation, a truckload of frozen meat in containers will be received at the meat processing plant and a sample container of frozen meat will be removed from each pallet of meat containers as the same are removed from the truck. These sample containers, of which there may be 50 per truck, are then transported to the testing area or laboratory where the sample containers are to be tested. At this stage, the apparatus 10 of the present invention comes into use. The container 21 is prepared for testing by having the portion of the container covering the surface to be drilled removed so as not to contaminate the meat samples with the container material. The container 21 is placed upon table 12 with the outer vertical edges of the front surface of the frozen block to be drilled resting against inner vertical surfaces of the upright abutment members 22, 23 facing the operator and as best illustrated by FIGS. 4 and 5.

Once container 21 has been prepared and placed upon table 12 in the manner described, clamps 13, 14 are moved into the horizontal position seen in FIG. 5 and pads 37 are pressed in tight contact against the middle of the outer vertical surface of container 21 and which due to the resiliency of the container covering will cause the otherwise loosely mounted sleeves 35 to bind on rods 26, 27 and thereby effectively clamp container 21 between pads 37 and abutment members 22, 23. Next, selector switch 111 is moved to the on position and start button 112 is pressed to initiate the operation of drill motor 100, hydraulic pump 70 and hydraulic valve 72 in the manner previously described. As carriage 15 moves toward the exposed surface of the frozen meat block to be drilled, the drill bit unit 16 will be moved in the same direction and the five sets of drill bit flutes 107 will begin to penetrate simultaneously into the meat block within container 21. As flutes 107 move into the meat block, bits of meat are removed from the block and are directed downward into guide funnel 120 and into a bag 122 suspended by suitable means below and from funnel 120. During this drilling operation, five bores in the embodiment illustrated are taken in each block. Once the trip arm 66 of limit switch 65 contacts the adjustment block 68, magnetic starter 115 will be opened, drill motor 100 will stop and cause rotation of bits 107 to stop. At the same time, carriage 15 will be caused to automatically reverse its direction and return carriage 15 and drill bit unit 16 to their respective start positions. While not entirely predictable, it has been found that in most instances, the clamps 13, 14 will automatically release once the drill bit unit 16 has been fully withdrawn from container 21. In the event clamps 13, 14 do not automatically release, the operator simply rotates the clamps 13, 14 back to their vertical position as seen in FIG. 1 and which allows the sampled container 21 to be removed for replacement by a new container 21 and a repetition of the same sampling operation.

It will be understood that the foregoing operation will be repeated until all of the sample containers 21 from the complete truckload of frozen meat have been sampled in the manner described. The meat removed by the test drillings will be collected in the respective bags 122 and taken to an appropriate test area for mixing and running of appropriate tests to determine the fat content of the frozen meat in the particular truckload of meat being sampled.

Figure 1:
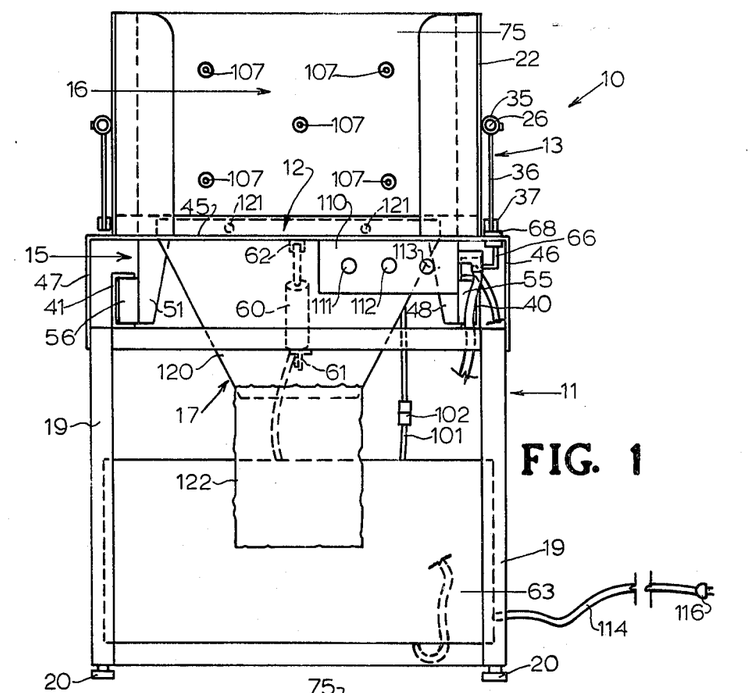
FIG. 1 is a front elevation view of the apparatus for removing samples from frozen meat blocks according to the method of the present invention but without a container and with the clamps in a loose non-clamping position.
Figure 2:
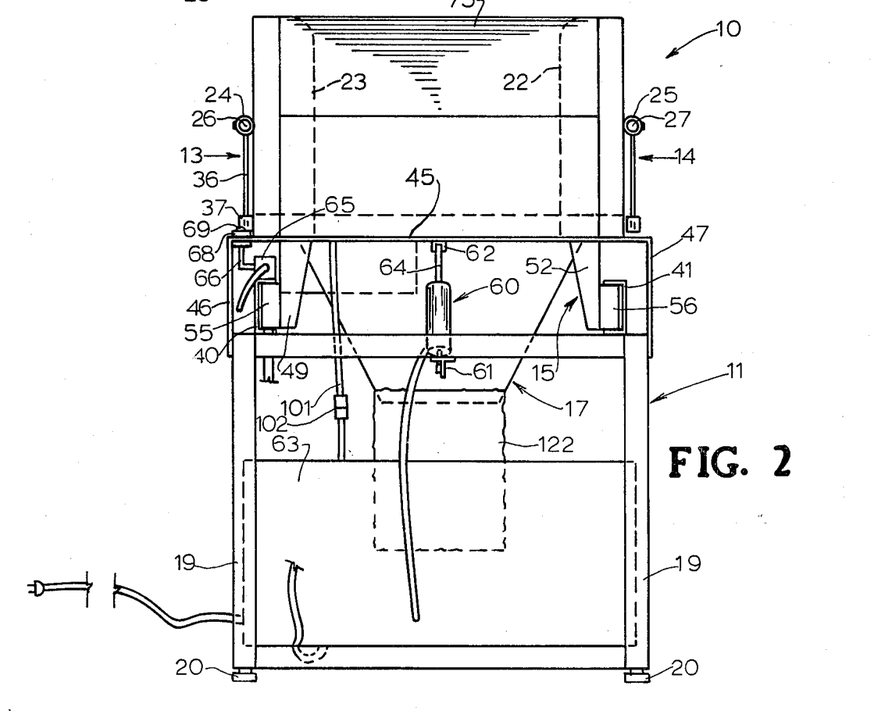
FIG. 2 is a rear elevation view of the apparatus of FIG. 1.

While in the embodiment described, a set of five drills have been depicted and in the space pattern shown in FIG. 1, it should be understood that the specifications for the number of drills, the depth of drilling, the size of drills, the spacing of the drills, and like considerations, are all determined by manufacturers and suppliers and vary from one to another. Therefore, it is contemplated that in the event of a change in such specifications that the method and apparatus of the invention will be modified accordingly to meet such new specifications. While the typical frozen meat block is expected during sampling to be enclosed by a "container" on all sides except on the exposed side being drilled, it is recognized that the entire container could, of course, be removed. In such event, the claims hereafter set forth would treat the "container" as being the sides of the frozen block and it would be such exposed sides that would be clamped and supported directly as hereafter claimed. Also to be understood is that container sizes may vary from shipment to shipment. However, it can be seen that any container suited to the abutment and clamping structure described could be drilled and sampled by the apparatus and method of the invention. In one embodiment, the apparatus was designed to accommodate containers having a width of 18 inches to 26 inches and a thickness of 3 inches to 10½ inches. A wide range of sizes were clamped and drilled successfully.

What is claimed is:

1. An apparatus for removing and collecting samples simultaneously drilled from plural-spaced locations in one exposed side face of a frozen meat block having its other sides normally enclosed by a container within some predetermined range of dimensions of size, comprising:
   (a) a support frame;
   (b) a table fixed to said frame adjacent a front portion thereof and providing a flat surface for supporting one side of said frozen block while retained thereon;
   (c) abutment means extending above said table and arranged to receive in abutting relation outer vertical edges of said exposed side face;
   (d) releasable clamping means mounted on said table and providing means for releasably clamping said container supported on one side on said table and wherein the said exposed side face of the frozen meat block contained therein is rigidly fixed in a substantially vertical plane for drilling, said clamping means comprising a pair of arm members loosely and rotatably mounted at one end thereof on forwardly extending horizontal rod members supported above said table on either side of the space occupied by said frozen meat block container when secured on said table, said arm members having at the opposite ends thereof pad means providing surfaces for engaging an outer side surface of said container parallel to said block plane being drilled, said arm members being adapted for opposed horizontal positioning and to bind on said rod members as said pad means are pressed against said container outer side surface during drilling of said block and to be freely releasable therefrom upon completion of said drilling;
   (e) carriage means mounted on said frame for travel between a forward advanced position proximate the vertical plane of the exposed side face of said frozen meat block and a retracted position remote therefrom, the extent of said carriage travel conforming to a desired depth of drilling said samples according to the desired quantity thereof;
   (f) directionally controllable drive means mounted on said frame for moving said carriage means between said advanced and retracted positions at a selected speed;
   (g) multiple drill means including drive means therefor mounted on said carriage means and movable therewith towards and from said block vertical plane, said drill means providing a plurality of drills spaced apart in a predetermined fixed pattern and having the longitudinal axis of the flute portions thereof parallel, extending forwardly and in a perpendicular relation to said block vertical plane, said drills being arranged to simultaneously drill said block to some predetermined depth at each drill location as said carriage moves to said advanced position with said container secured by said clamping means;
   (h) collecting means located below said drill means and adapted to collect meat particles drilled by said drills from the exposed side of said frozen meat block during movement of said carriage means to said advanced position; and
   (i) control means operative to actuate said carriage and drill drive means and cause said drills to rotate during advancement of said carriage and said carriage means to cycle from said retracted position to said advanced position and back to said retracted position enabling samples to be collected in said collecting means simultaneously from said locations drilled by said drill means.

2. The apparatus of claim 1 wherein said directionally controllable drive means for moving said carriage means between said advanced and retracted position comprises a hydraulically-operated piston/cylinder mechanism, said drive means for said drill means comprises an electric motor belt drive mechanism and said control means includes electrically operated valve means and limit switch means operated in coordination with movements of said carriage means to control said piston/cylinder and motor belt drive mechanisms.

3. An apparatus for removing and collecting samples simultaneously drilled from plural-spaced locations in one exposed side face of a frozen meat block having its other sides normally enclosed by a container within some predetermined range of dimensions of size, comprising:

(a) a support frame;

(b) a support table made integral with said frame adjacent a front portion thereof and providing a flat surface for supporting one side of said container while retained thereon;

(c) a pair of upright abutment members made integral with rear outer edge portions of said support table and providing vertical abutment surfaces adapted for receiving and vertically aligning an exposed said side face of said block by contact with the outermost vertical frontal edge surfaces thereof;

(d) releasable clamping means having a pivotal, adjustable and loose mounting arrangement positioned forward of said abutment surfaces and adapted to clamp a container within a range of varying size while resting on said table with the said exposed side face of said block held against said abutment surfaces during drilling and having clamping surfaces adapted to engage the outer side surface of the container parallel to the said exposed side face of the block being drilled, said mounting arrangement being adapted to bind in clamping position during drilling and to automatically release and free the container from said clamping means for removal from said table at the determination of said drilling;

(e) movable carriage means mounted on said frame for travel between a forward advanced position proximate the vertical plane of said exposed side face of said block and a retracted position remote therefrom, the extent of said movable carriage travel conforming to a desired depth of drilling of said samples and according to the desired quantity thereof;

(f) directionally and speed controllable drive means mounted on said support frame for moving said movable carriage means between said advanced and retracted positions at a selected speed;

(g) multiple drill means including drive means therefor mounted on said movable carriage means and movable therewith towards and away from said exposed side face of said block, said multiple drill means providing a plurality of drills spaced apart in a predetermined fixed pattern and having the longitudinal axis of the flute portions thereof parallel, extending forwardly and in a perpendicular relation to the plane of said block exposed side face, said drills being arranged to simultaneously penetrate said block exposed side face to some predetermined depth at each drill location as said movable carriage travels to said advanced position with said container secured by said clamping means;

(h) collecting means located below said drill means, said collecting means being removably suspended from said movable carriage means and adapted to travel with said movable carriage and said drill means, said collecting means adapted to collect meat particles removed by said drills from said exposed side face of said block during travel of said movable carriage means to said advanced position; and (i) control means operative to actuate said movable carriage and said drill drive means and cause said drills to rotate during advancement of said movable carriage and said movable carriage means to cycle from said retracted position to said advanced position and back to said retracted position enabling samples to be removed from said block and collected in said collecting means simultaneously from each said location drilled by said drill means.

4. A method for testing frozen meat blocks prior to use by the processor comprising:

(a) removing at random a group of containers of frozen meat blocks from a load of meat shipped to the processor and exposing one side face of each block so removed;

(b) releasably clamping each container so removed in succession on a fixed table forming part of a drilling machine having carriage mounted, powered, multiple, spaced-apart, axially parallel drills with uncovered flute portions facing and with the axis of said drills oriented perpendicular to the respective exposed side face of the block being drilled and with the clamping means being adapted for loosely holding a selected size of container and corresponding block between fixed abutments and pivotal clamps adapted to secure the container during drilling and to automatically pivot and release the container at the termination of drilling;

(c) sampling all the blocks in the group in succession by taking multiple samples simultaneously from each said block so clamped by moving said carriage in a cycle towards and away from said exposed side face to cause said uncovered flute portions to drill to some predetermined depth in and to remove meat samples from said block and after each cycle allowing said pivotal clamps to pivot under the force of gravity to release said container and the block contained therein for removal from said table;

(d) allowing said samples to be collected in a common container until said samples have been taken from all the blocks in said group of containers so removed;

(e) removing said common container and collected samples;

(f) combining all collected samples into one unit; and (g) removing selected portions of said unit for testing of said meat to determine the average fat content of the load of frozen meat delivered to the processor.

5. The method of claim 4 including moving said container while supported on said carriage during each said cycle.

6. An apparatus for removing and collecting samples simultaneously drilled from plural-spaced locations in one exposed side face of a frozen meat block having its other sides normally enclosed by a container within some predetermined range of dimensions of size, comprising:

(a) a support frame;

(b) a table fixed to said frame adjacent a front portion thereof and providing a flat surface for supporting one side of said frozen block while retained thereon;

(c) abutment means extending above said table and arranged to receive in abutting relation outer vertical edges of said exposed side face;

(d) manually positionable and releasable clamping means mounted above said table and providing means for loosely engaging an outer side portion of said container opposite said exposed side face and for releasably clamping said outer vertical edges of said container while supported on one side on said table against said abutment means to fix the portion of said exposed side face of the frozen block between said edges in an unobstructed substantially vertical plane accessible for drilling and being adapted for binding in position during drilling and for being automatically and freely releasable upon completion of said drilling to allow removal of said container from said table;

(e) carriage means mounted on said frame for travel between a forward advanced position corresponding to some predetermined depth of drilling into said exposed side face of said block and a drill retracted position remote therefrom;

(f) directionally controllable drive means mounted on said frame for moving said carriage means between said advanced and retracted positions at a selected speed;

(g) multiple drill means including drive means therefor mounted within a housing carried by said carriage means and movable therewith towards and from said block vertical plane, said drill means providing a plurality of drills having unshrouded flute portions spaced apart in a predetermined fixed pattern extending through a vertical side plate of said housing and having the longitudinal axis of said flute portions parallel, extending forwardly towards and in a perpendicular relation to said block vertical plane, said drills being arranged to simultaneously drill said block to said predetermined depth at each drill location as said carriage moves to said advanced position with said container secured by said clamping means;

(h) collecting means located on said carriage means below said drill means and adapted to collect meat particles drilled by said drills from said exposed side of said block during movement of said carriage means to said advanced position; and (i) control means operative to actuate said carriage and drill drive means and cause said drills to rotate during advancement of said carriage and said carriage means to cycle from said retracted position to said advanced position and back to said retracted position enabling samples to be collected in said collecting means simultaneously from said locations drilled by said drill means.

* * * * *

UNITED STATES PATENT AND TRADEMARK OFFICE
CERTIFICATE OF CORRECTION

PATENT NO. : 4,149,414
DATED : April 17, 1979
INVENTOR(S) : Richard B. Walker

It is certified that error appears in the above-identified patent and that said Letters Patent are hereby corrected as shown below:

Column 1, line 24, the first occurrence of "and" should be deleted.

Column 2, line 55, "FIG. 5" should be --FIG. 4--.

Column 7, line 41, "enlosed" should be --enclosed--.

Signed and Sealed this

Tenth Day of July 1979

[SEAL]

Attest:

LUTRELLE F. PARKER
Attesting Officer    Acting Commissioner of Patents and Trademarks